United States Patent [19]

Kato et al.

[11] Patent Number: 5,723,665
[45] Date of Patent: Mar. 3, 1998

[54] ETHENYL AMIDE COMPOUND PRODUCTION PROCESS

[75] Inventors: Shozo Kato; Shigeo Tamura; Toshio Kitajima; Noriyuki Fukada, all of Tokuyama, Japan

[73] Assignee: Tokuyama Corporation, Yamaguchi-ken, Japan

[21] Appl. No.: 749,542

[22] Filed: Nov. 15, 1996

[30] Foreign Application Priority Data

Nov. 15, 1995 [JP] Japan .................................. 7-297099

[51] Int. Cl.$^6$ .................................................. C07C 231/02
[52] U.S. Cl. .......................... 564/142; 546/336; 548/561; 549/77; 549/493; 564/133; 564/143; 564/205; 564/209; 564/210; 564/211
[58] Field of Search ........................... 564/133, 142, 564/143, 205, 209, 210, 211; 546/336; 548/561; 549/77, 493

[56] References Cited

U.S. PATENT DOCUMENTS 4,599,448  7/1986  Thomas .................................. 564/214
4,600,433  7/1986  Alt ........................................ 71/118
4,895,587  1/1990  Kato et al. ............................ 71/90

FOREIGN PATENT DOCUMENTS 1 491 814  11/1977  European Pat. Off. .
0 065 712  12/1982  European Pat. Off. .
0 206 251  12/1986  European Pat. Off. .
0 375 387  6/1990   European Pat. Off. .
61-293956  12/1986  Japan .

*Primary Examiner*—Shailendra Kumar
*Attorney, Agent, or Firm*—Birch, Stewart, Kolasch & Birch, LLP

[57] ABSTRACT

A process for producing an ethenyl amide compound, which comprises reacting a Schiff base compound having a carbon atom adjacent to a carbon atom constituting an imino group and at least one hydrogen atom on the carbon atom with an acylhalide at a reduced pressure while removing by-produced hydrogen halide by distillation to produce an ethenyl amide compound having an amide bond in the molecule and a double bond between carbons at α-position and β-position with respect to the nitrogen atom of the amide bond.

11 Claims, No Drawings

5,723,665

ETHENYL AMIDE COMPOUND PRODUCTION PROCESS

DETAILED DESCRIPTION OF THE INVENTION

This invention relates to a process for producing an ethenyl amide compound. More specifically, it relates to a process for producing a high-purity ethanol amide compound, which is useful, for example, as a herbicide, through a reaction between a Schiff base compound and an acylhalide at a high yield.

A process for producing an ethenyl amide compound through a reaction between a Schiff base compound and an acylhalide has already been known. U.S. Pat. No. 4,600,433 discloses a process for producing an ethenyl amide compound by reacting a Schiff base compound and an acylchloride in a toluene solvent at ordinary pressure. However, an ethenyl amide compound having a desired purity cannot be obtained by the above process depending on kinds of the substituents of the Schiff base compound and an acylhalide and it is necessary to purify an ethenyl amide compound by such operation as distillation or re-crystallization.

The inventors of the present invention have already proposed in the Laid-open Japanese Patent Application No. Sho 61-293956 a process for producing an ethenyl amide compound by carrying out the reaction in the presence of a hydrogen halide scavenger in a reaction system at ordinary pressure.

However, to obtain an object ethenyl amide compound having a desired purity by the prior art including our proposal described above, a by-product derived from the use of the hydrogen halide scavenger must be removed by filtration, solvent extraction or the like after the reaction. In addition, the obtained ethenyl amide compound must be purified by such operation as distillation or re-crystallization. These operations are not preferred from an industrial viewpoint. For instance, to carry out a re-crystallization operation on an industrial scale, it requires a great deal of labor and long time. To purify the object ethenyl amide compound by distillation, distillation must be carried out at a degree of vacuum as high as 133 Pa or less. Otherwise, purification by distillation cannot be accomplished due to thermal decomposition. To carry out distillation at a high vacuum degree of 133 Pa or less on an industrial scale requires a great deal of labor and long time as in the case of re-crystallization. From this point of view, a more simple industrial process for producing an ethenyl amide compound has been ardently desired.

It is therefore an object of the present invention to provide a novel process for producing an ethenyl amide compound.

It is another object of the present invention to provide a process for carrying out a reaction for producing ethenyl amide from a Schiff base and an acylhalide at a reduced pressure, preferably while introducing an inert gas into a reaction system.

It is still another object of the present invention to provide a process for producing high-purity ethenyl amide at a high yield.

The above and other objects and advantages of the present invention will become apparent from the following description.

According to the present invention, the above objects and advantages of the present invention are attained by a process for producing an ethenyl amide compound, which comprises reacting a Schiff base compound having a carbon atom adjacent to a carbon atom constituting an imino group and at least one hydrogen atom on this carbon atom with an acylhalide at a reduced pressure while removing by-produced hydrogen halide to produce an ethenyl amide compound having an amide bond in the molecule and a double bond between carbons at α-position and β-position with respect to the nitrogen atom of the amide bond in a reaction system.

The Schiff base compound used in the present invention is a compound having a carbon atom adjacent to a carbon atom constituting an imino group forming the basic skeleton of the Schiff base and a hydrogen atom on this carbon atom.

In the process of the present invention, the Schiff base compound and the acylhalide are reacted with each other at a reduced pressure. At this time, hydrogen halide by-produced by this reaction is removed from the reaction system by distillation and an object ethenyl amide compound is allowed to remain in the reaction system.

The range of the reduced pressure in the process of the present invention is preferably from $1.3 \times 10^2$ to $1 \times 10^5$ Pa, more preferably from $1.3 \times 10^3$ to $6.7 \times 10^4$ Pa. It is not always necessary to keep a constant pressure throughout the reaction. Rather, favorable results can be obtained when the pressure is suitably changed according to circumstances.

When the reaction is carried out at a pressure higher than $1 \times 10^5$ Pa, it is more likely that the hydrogen halide by-produced in the reaction reacts with the Schiff base as a starting material to consume the starting material or delay the reaction to increase the amount of impurities.

The process of the present invention can be carried out in the presence of an inert organic solvent as will be described hereinafter. When the reaction is carried out at a reduced pressure in this case, the boiling temperature of the reaction solvent is lowered, and the hydrogen halide by-produced by the reaction goes away swiftly from the reaction system together with the gasified solvent, thereby increasing the reaction rate, which makes it possible to suppress an undesired side reaction caused by the hydrogen halide which is a strong acidic compound. Therefore, an object ethenyl amide compound having a higher purity can be obtained more efficiently. Means for reducing the pressure of the reaction system is not particularly limited. For example, means for reducing the pressure using a known apparatus such as a hydraulic rotary vacuum pump, diaphragm vacuum pump or water-jet pump can be used without hindrance.

Further, when the reaction is carried out at a reduced pressure while introducing an inert gas into the reaction system, favorable results in terms of yield and purity can be obtained. Illustrative examples of the inert gas include nitrogen, argon and helium gases and a carbon dioxide gas, out of which nitrogen gas is the most preferred from an industrial point of view.

To introduce the inert gas, the gas may be introduced into a gaseous phase of the reaction system or blown into a reaction mixture. In the latter case, better results are obtained in most cases.

The rate of introducing (flow rate of) the inert gas is generally 0.01 to 800 l/hr, preferably 0.1 to 80 l/hr. It is not always necessary to keep a constant flow rate throughout the reaction. Good results are obtained when the flow rate is suitably changed according to circumstances in most cases.

More specifically, carrying out a reaction at a reduced pressure is intended not only to accelerate the reaction by removing the hydrogen halide by-produced in the reaction system from the reaction system efficiently but also to improve the reaction yield and purity of the object substance by suppressing a side reaction for formation of an adduct from the hydrogen halide and Schiff base which is one of the starting materials or by decomposing the by-produced adduct. It has been revealed that the introduction of the inert gas makes more remarkable the function and effect of pressure reduction as described above.

In the present invention, the acylhalide is preferably used in an amount of 1 to 1.3 moles per one mole of the Schiff base compound.

The inert organic solvent can be present in the reaction. As the inert organic solvent, those having a boiling point of 35° to 200° C. at ordinary pressure are preferred. Known inert organic solvents such as benzene, toluene, xylene, hexane, heptane, chloroform, carbon tetrachloride and the like all of which do not react with starting materials are advantageously used as the organic solvent.

A method for charging the both materials in performing the reaction is not particularly limited. For example, one of the starting materials is first charged into the reactor and then, the other starting material is gradually added at a reduced pressure. Or, one of the starting materials is first charged into the reactor and a solvent later described is added thereto to completely dissolve it to prepare a solution or to dissolve it to some extent to prepare a solution in which a few or most part of the material remains undissolved, and then the other starting material is gradually added at a reduced pressure. Alternatively, the both starting materials and the reaction solvent may be charged together into the reactor from the beginning.

The reaction temperature is generally 40° to 100° C. and the pressure and temperature are desirably set such that the reaction system is brought under reflux. It is not always necessary to keep a constant reaction temperature so long as good results are obtained. When the reaction is carried out under reflux, the above organic solvent which dissolves all of the starting materials and has a lower boiling point than that of the starting materials is added to the reaction system, and pressure and temperature are set such that the solvent is brought under reflux if all of the starting materials, the Schiff base compound and acylhalide, do not have a boiling point of 100° C. or less at a pressure of $1.3 \times 10^2$ or more but less than $1 \times 10^5$ Pa.

Since it is difficult to carry out the reaction by keeping the reaction pressure constant when the solvent is not used, it is preferred to set pressure at a higher value in an initial stage and then gradually to lower values as the reaction proceeds. When the solvent is used, it is easily removed after the completion of the reaction at a pressure of $1.3 \times 10^2$ or more but less than $1 \times 10^5$ Pa depending on type of the solvent. The main feature of the present invention is that the residue after the solvent is removed can be used as an object ethenyl amide compound directly without further purification.

In the present invention, the Schiff base compound is preferably represented by the following formula (1):

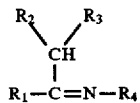

(1)

wherein $R_1$ is a substituted or unsubstituted aryl group having 6 to 14 carbon atoms or a substituted or unsubstituted heteroaryl group having 3 to 8 carbon atoms containing one or two hereto atoms selected from the group consisting of oxygen atom, sulfur atom and nitrogen atom, $R_2$ and $R_3$ are the same or different and each is a hydrogen atom or an alkyl group, or may be bonded together to form a ring, and $R_4$ is a substituted or unsubstituted alkyl group having 1 to 12 carbon atoms, a substituted or unsubstituted alkenyl group having 2 to 12 carbon atoms, a substituted or unsubstituted alkinyl group having 2 to 12 carbon atoms, a substituted or unsubstituted aryl group having 6 to 14 carbon atoms, a substituted or unsubstituted heteroaryl group having 3 to 8 carbon atoms, a substituted or unsubstituted cycloalkyl group having 3 to 6 carbon atoms, a substituted or unsubstituted cycloalkenyl group having 4 to 6 carbon atoms, or a substituted or unsubstituted heterocycloalkyl group having 4 to 5 carbon atoms.

Illustrative examples of the unsubstituted aryl group having 6 to 14 carbon atoms and unsubstituted heteroaryl group, represented by $R_1$ include phenyl, anthranyl and phenanthrenyl groups and those of the unsubstituted heteroaryl group represented by $R_1$ include furyl, thienyl, pyrrolyl, pyridyl, pyrimidinyl, benzofuryl, benzothienyl, indolyl, quinolyl, thiazolyl, pyrazolyl, oxazolyl and benzoxazolyl groups.

Illustrative examples of the substituent of the substituted aryl group and substituted heteroaryl group, represented by $R_1$ include alkyl groups having 1 to 6 carbon atoms such as methyl, ethyl and propyl groups; halogen atoms such as chlorine, bromine, iodine and fluorine atoms; alkoxy groups having 1 to 6 carbon atoms such as methoxy, ethoxy and propoxy groups; alkylthio groups having 1 to 6 carbon atoms such as methylthio, ethylthio and propylthio groups; a cyano group; a nitro group; and an amino group.

Specific examples of the substituted aryl group and substituted heteroaryl group include methylphenyl, ethylphenyl, propylphenyl, butylphenyl, hexylphenyl, dimethylphenyl, methyl(ethyl)phenyl, ethyl(propyl)phenyl, chlorophenyl, bromophenyl, fluorophenyl, dichlorophenyl, methoxyphenyl, ethoxyphenyl, propoxyphenyl, dimethoxyphenyl, cyanophenyl, nitrophenyl, chloro(methyl)phenyl, methyl(methoxy)phenyl, methylthiophenyl, (trifluoromethyl)phenyl, (dimethyl)aminophenyl, chloro(nitro)phenyl, methylnaphthylnaphthyl, chloronaphthyl, methoxynaphthyl, dimethylnaphthyl, methylfuryl, methoxythienyl, chlorothienyl, methylthienyl, methylpyrrolyl, chloropyrrolyl, methylpyridyl, chloropyridyl, dimethoxypyrimidinyl, methylpyrimidinyl, chloropyrimidinyl, methylbenzofuryl, methoxybenzofuryl, chlorobenzofuryl, methylbenzothienyl, methylindolyl, methylquinolyl, methylthiazolyl, methylpyrazolyl, methyloxazolyl and methylbenzoxazolyl Groups and the like.

The alkyl group independently represented by $R_2$ and $R_3$ is not particularly limited, and any of known alkyl groups may be used. Generally speaking, a linear or branched alkyl group having 1 to 12 carbon atoms is advantageously used. Specific examples of the alkyl group include methyl, ethyl, propyl, butyl, pentyl and hexyl groups and the like. The ring formed when $R_2$ and $R_3$ are bonded together is a cycloalkyl ring having 3 to 8 ring-member carbon atoms such as cyclopentyl or cyclohexyl.

Illustrative examples of the unsubstituted alkyl group having 1 to 12 carbon atoms represented by $R_4$ include methyl, ethyl, propyl, butyl, hexyl, heptyl, octyl, nonyl and decyl groups and the like. Similarly illustrative examples of the unsubstituted alkenyl group having 2 to 12 carbon atoms include ethenyl, propenyl, butenyl, hexenyl and octenyl groups and the like. Those of the unsubstituted alkinyl group having 2 to 12 carbon atoms include propynyl and butynyl groups and the like. Those of the unsubstituted aryl group include phenyl, naphthyl, anthranyl and phenanthrenyl groups and the like. Those of the unsubstituted heteroaryl group having 3 to 8 carbon atoms include furyl, thienyl, pyrrolyl, pyridyl, pyrimidinyl, benzofuryl, benzothienyl, indolyl, quinolyl, thiazolyl, pyrazolyl, oxazolyl and benzoxazolyl groups and the like. Those of the unsubstituted cycloalkyl group include cyclopropyl, cyclobutyl, cyclopentyl, cyclohexyl and cycloheptyl groups and the like. Those of the unsubstituted cycloalkenyl group include cyclopentenyl and cyclohexenyl groups and the like. Those of the unsubstituted heterocycloalkyl group having 4 to 5 carbon atoms include tetrahydrofuryl, tetrahydrothienyl and pyrrolidyl groups and the like.

Examples of the substituent of the substituted aryl group, substituted heteroaryl group, substituted cycloalkyl group, substituted cycloalkenyl group and substituted heterocycloalkyl group, represented by $R_4$ include alkyl groups having 1 to 6 carbon atoms such as methyl, ethyl and propyl groups; halogen atoms such as chlorine, bromine, iodine and fluorine atoms; alkoxy groups having 1 to 6 carbon atoms such as methoxy, ethoxy and propoxy groups; alkylthio groups having 1 to 6 carbon atoms such as methylthio, ethylthio and propylthio groups; a cyano group; a nitro group; and an amino group.

Specific examples of the substituted aryl group, substituted heteroaryl group, substituted cycloalkyl group, substituted cycloalkenyl group and substituted heterocycloalkyl group include methylphenyl, ethylphenyl, propylphenyl, butylphenyl, hexylphenyl, dimethylphenyl, methyl(ethyl) phenyl, ethyl(propyl)phenyl, chlorophenyl, bromophenyl, fluorophenyl, dichlorophenyl, methoxyphenyl, ethoxyphenyl, propoxyphenyl, dimethoxyphenyl, cyanophenyl, nitrophenyl, chloro(methyl)phenyl, methyl (methoxy)phenyl, methylthiophenyl, (trifluoromethyl) phenyl, (dimethyl)aminophenyl, chloro(nitro)phenyl, methylnaphthylnaphthyl, chloronaphthyl, methoxynaphthyl, dimethylnaphthyl, methylfuryl, methoxythienyl, chlorothienyl, methylthienyl, methylpyrrolyl, chloropyrrolyl, methylpyridyl, chloropyridyl, dimethoxypyrimidinyl, methylpyrimidinyl, chloropyrimidinyl, methylbenzofuryl, methoxybenzofuryl, chlorobenzofuryl, methylbenzothienyl, methylindolyl, methylquinolyl, methylthiazolyl, methylpyrazolyl, methyloxazolyl, methylbenzoxazolyl, chloroethenyl, bromoethenyl, chloropropenyl, chlorohexenyl, methylcyclopropyl, ethylcyclopropyl, chlorocyclopropyl, methoxycyclopropyl, methylcyclopentyl, chlorohexyl, methylcyclohexyl, methylcyclopentenyl, chlorocyclohexenyl, methylcyclohexenyl, N-methylpyrrolidyl and N-ethylpyrrolidyl groups and the like.

Illustrative examples of the substituent of the substituted alkyl group, substituted alkenyl group and substituted alkinyl group, represented by $R_4$ include halogen atoms such as chlorine, bromine, iodine and fluorine atoms; alkoxy groups such as methoxy, ethoxy and propoxy groups; alkylthio groups such as methylthio, ethylthio and propylthio groups; alkoxyalkyl groups; a cyano group; a nitro group; and an amino group.

Specific examples of the substituted alkyl group include fluoromethyl, trifluoromethyl, chloromethyl, chloroethyl, bromoethyl, chloropropyl, chlorohexyl, methoxymethyl, methoxyethyl, methoxypropyl, methoxybutyl, ethoxymethyl, ethoxyethylol ethoxypropyl, butoxymethyl, butoxyethyl, phenoxymethyl, phenoxyethyl, cyanopropyl, cyanobutyl, nitroethyl, nitropropyl, ethylthiomethyl, propylthiomethyl, methylthioethyl, ethylthioethyl, N,N-diethylaminoethyl, N,N-diethylaminopropyl, phenylmethyl, phenylethyl, methoxythienylmethyl, methoxycarbonylmethyl, methoxycarbonylethyl and ethoxycarbonylethyl groups and the like. Specific examples of the substituted alkenyl group include chloropropenyl, cyanobutenyl and methoxypentenyl groups and the like. Specific examples of the substituted alkinyl group include chloropentynyl, ethoxybutynyl and nitrohexynyl groups and the like.

There exist various position isomers in most of the compounds having the above groups, and such isomers may be used in the present invention without restriction. For example, isomers of methylphenyl group are o-methylphenyl, m-methylphenyl and p-methylphenyl groups and those of butyl group are n-butyl, sec-butyl and tert-butyl groups.

Further, the substituents are not limited to the above illustrative examples and any substituent may be suitably used as required if an ethenyl amide compound having the object basic structure can be obtained therefrom by the production process of the present invention.

The Schiff base represented by the above formula (1) may be exemplified by compounds listed in Table 1 below.

TABLE 1

| Compound No. | $R_1$ | $R_2$ | $R_3$ | $R_4$ |
|---|---|---|---|---|
| 1S | 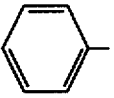 | H | H | 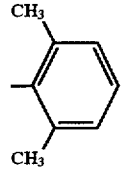 |
| 2S | 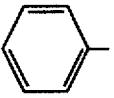 | $CH_3$ | $CH_3$ | $-CH_2CH_2OCH_3$ |
| 3S | 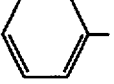 | H | $CH_3$ | $-CH_2CH_2OCH_3$ |

TABLE 1-continued

| Compound No. | R₁ | R₂ | R₃ | R₄ |
|---|---|---|---|---|
| 4S | phenyl | CH₃ | CH₃ | —CH₂CH₂OEt |
| 5S | 4-CH₃-phenyl | CH₃ | CH₃ | —(CH₂)₃OCH₃ |
| 6S | 3-Cl-phenyl | H | H | —(CH₂)₄CH₃ |
| 7S | 4-CH₃O-phenyl | CH₃ | H | phenyl |
| 8S | 4-CH₃S-phenyl | CH₃ | Et | —(CH₂)₃OEt |
| 9S | 4-NC-phenyl | CH₃ | CH₃ | —(CH₂)₃OPr |
| 10S | naphthyl | Et | H | —CH₂-phenyl |
| 11S | 2-pyridyl | CH₃ | CH₃ | —Et |
| 12S | 2-thienyl | CH₃ | CH₃ | —(CH₂)₃CH₃ |
| 13S | 2-furyl | CH₃ | CH₃ | —CH₂CH₂-phenyl |
| 14S | phenyl | H | H | 2,4-dichlorophenyl |
| 15S | 2,4-dimethylphenyl | CH₃ | H | —CH₂OCH₃ |

TABLE 1-continued

| Compound No. | R₁ | R₂ | R₃ | R₄ |
|---|---|---|---|---|
| 16S | 1-methylpyrrol-2-yl | H | H | 2,6-dimethylphenyl |
| 17S | 4-bromophenyl | $CH_3$ | $CH_3$ | 1-naphthyl |
| 18S | 4-isopropylphenyl | H | $-CH_2CH_2CH_3$ | $-(CH_2)_2SCH_3$ |
| 19S | 4-methoxythiophen-2-yl | H | H | $-CH_2CH_2CO_2Et$ |
| 20S | 4-nitrophenyl | | $-(CH_2)_5-$ | Et |

In the present invention, the acylhalide is preferably represented by the following formula (2):

$$R_5COX \quad (2)$$

wherein $R_5$ is a substituted or unsubstituted alkyl group having 1 to 12 carbon atoms, a substituted or unsubstituted aryl group having 6 to 14 carbon atoms, or a substituted or unsubstituted heteroaryl group having 3 to 8 carbon atoms containing one or two hetero atoms selected from the group consisting of oxygen atom, sulfur atom and nitrogen atom, and X is a halogen atom.

Illustrative examples of the above substituted or unsubstituted alkyl group, substituted or unsubstituted aryl group or substituted or unsubstituted heteroaryl group are the same as those provided for $R_4$ above.

The halogen atom represented by X is selected from chlorine, bromine, fluorine and iodine, out of which chlorine is preferred from an industrial point of view.

The acylhalide represented by the above formula (2) may be exemplified by compound listed in Table 2 below.

TABLE 2

| Compound No. | R₅ | X | Compound No. | R₅ | X | Compound No. | R₅ | X |
|---|---|---|---|---|---|---|---|---|
| 1C | $CH_3$ | Cl | 7C | 4-methoxyphenyl | Br | 13C | Et | Cl |
| 2C | $-CH_2Br$ | Cl | 8C | $-CH_2OCH_3$ | Cl | 14C | $CF_3$ | Cl |
| 3C | isopropyl | Cl | 9C | $-CH_2Cl$ | Br | 15C | $-CH_2$-phenyl | Cl |

TABLE 2-continued

| Compound No. | R₅ | X | Compound No. | R₅ | X | Compound No. | R₅ | X |
|---|---|---|---|---|---|---|---|---|
| 4C | —CHCl₂ | Cl | 10C | —CH₂Cl | Cl | 16C |  | Cl |
| 5C | (phenyl) | Cl | 11C | —CH₂Br | Br | 17C | —CH₂CH(CH₃)CH₃ | Cl |
| 6C | (4-Et-phenyl) | Cl | 12C | —CH₂Cl | I | 18C | —CH₂CH₂Cl | Cl |

The object ethenyl amide compound obtained by the process of the present invention has an amide bond in the molecule and a double bond between carbons at α-position and β-position with respect to the nitrogen atom of the amide bond.

A typical ethenyl amide compound is represented by the following general formula (3).

$$\begin{array}{c} R_2 \quad R_3 \\ \diagdown \;\; \diagup \\ C \quad\quad R_4 \\ \| \quad\quad \diagup \\ R_1 - C - N \\ \quad\quad\;\; \diagdown \\ \quad\quad\quad COR_5 \end{array} \quad (3)$$

In the above general formula (3), $R_1$, $R_2$, $R_3$, $R_4$ and $R_5$ are defined the same as in the above general formulas (1) and (2).

Illustrative examples of the ethenyl amide compound represented by the above formula (3) are obvious from the above examples of the Schiff base compound and the acylhalide.

It is known that the ethenyl amide compound obtained in the present invention is useful as an agricultural chemical, for example.

The ethenyl amide compound obtained by the process of the present invention is generally dark brown or light yellowish brown solid or viscous substance.

In addition to the object ethenyl amide compound, hydrogen halide is by-produced in an equimolar amount by the reaction of the present invention. According to the present invention, however, the removal of the by-produced hydrogen halide from the reaction system is promoted by carrying out a reaction at a reduced pressure. In a reaction at ordinary pressure, a by-product, which causes reduction of purity, is produced mainly by the function of the hydrogen halide. Therefore, the removal of the hydrogen halide is considered to be effective in the suppression of the side reaction.

The yield and purity of the object product obtained by the reaction of the present invention are both 90 to 99.9%. Therefore, even when a solvent is used during a reaction, the residue after the solvent is removed by distillation can be used directly as an object ethenyl amide compound without further purification.

The following Examples and Comparative Examples are given to further illustrate the present invention; however, it is to be understood that the present invention is not limited thereto.

EXAMPLE 1

N-(1-methylbenzylidene)-2',6'-dimethylaniline (45.7 g) was dissolved in toluene (100 ml) and chloroacetyl chloride (24.8 g) was dropped into the resulting solution under agitation at room temperature. After the completion of dropping, the solution was heated under reflux at a reduced pressure of 1.3×10⁴ Pa for 7 hours (reflux temperature of 70° C.). When toluene was removed by distillation at a reduced pressure of 2.7×10³ Pa after the completion of the reaction, 59.4 g of the reaction product was obtained. The reaction product was mainly composed of N-(1-phenyl)ethenyl-N-chloroaceto-2',6'-dimethylanilide and its yield was 100%. The purity of the main component of the reaction product was 99%.

EXAMPLE 2

N-(1-phenyl-2,2-dimethyl)ethylidene-2-methoxyethylamine (20.6 g) was dissolved in toluene (60 ml) and chloroacetyl chloride (15.2 g) was dropped into the resulting solution at room temperature. After the completion of dropping, the solution was heated under reflux at a reduced pressure of 1.3×10⁴ Pa for 4 hours (reflux temperature of 70° C.). When toluene was removed by distillation at a reduced pressure of 2.7×10³ Pa after the completion of the reaction, 27.6 g of the reaction product was obtained. The reaction product was essentially composed of N-(1-phenyl-2,2-dimethyl)ethenyl-N-chloroaceto-2-methoxyethylamide and its yield was 99%. The purity of the main component of the reaction product was 99%.

EXAMPLE 3

N-(1-phenyl-2-methyl)ethylidene-2-methoxyethylamine (26.3 g) was dissolved in toluene (40 ml) and chloroacetyl chloride (14.2 g) was dropped into the resulting solution at room temperature. After the completion of dropping, the solution was heated under reflux at a reduced pressure of 1.3×10⁴ Pa for 4 hours (reflux temperature of 70° C.). When toluene was removed by distillation at a reduced pressure of 2.7×10³ Pa after the completion of the reaction, 34.4 g of the reaction product was obtained. The reaction product was essentially composed of N-(1-phenyl-2-methyl)ethenyl-N-chloroaceto-2-methoxyethylamide and its yield was 97%. The purity of the main component of the reaction product was 99%.

EXAMPLE 4

N-(1-phenyl-2,2-dimethyl)ethylidene-2-ethoxyethylamine (43.8 g) was dissolved in toluene (50 ml) and chloroacetyl chloride (23.7 g) was dropped into the resulting solution at room temperature. After the completion of dropping, the solution was heated under reflux at a reduced pressure of 1.3×10⁴ Pa for 4 hours (reflux temperature of 70° C.). When toluene was removed by distillation at a reduced pressure of 2.7×10³ Pa after the completion of the reaction, 57.9 g of the reaction product was obtained. The reaction product was essentially composed of N-(1-phenyl-2,2-dimethyl)ethenyl-N-chloroaceto-2-ethoxyethylamide and its yield was 98%. The purity of the main component of the reaction product was 97%.

EXAMPLE 5

The following ethenyl amide compounds were prepared in the same manner as in Example 1. The reaction temperature, reaction pressure, kind of solvent, yield and purity of the product are shown in Table 3.

TABLE 3

| Example No. | Compound No. Schiff base compound | Compound No. Acyl halide | Reaction temperature (°C.) | Reaction pressure × 10⁴ Pa | Solvent | Yield of product of formula (3) (%) | Purity of product of formula (3) (%) |
|---|---|---|---|---|---|---|---|
| 5-1 | 5S | 1C | 80 | 2.60 | — | 96 | 97 |
| 5-2 | 6S | 2C | 50 | 3.60 | Benzene | 99 | 96 |
| 5-3 | 7S | 3C | 80 | 4.07 | Toluene | 97 | 96 |
| 5-4 | 8S | 4C | 60 | 1.91 | Toluene | 96 | 94 |
| 5-5 | 9S | 5C | 70 | 1.03 | Xylene | 98 | 98 |
| 5-6 | 10S | 6C | 80 | 1.57 | Xylene | 100 | 97 |
| 5-7 | 11S | 7C | 70 | 2.76 | Toluene | 95 | 95 |
| 5-8 | 12S | 8C | 75 | 3.29 | Toluene | 95 | 92 |
| 5-9 | 13S | 9C | 40 | 2.33 | Benzene | 92 | 93 |
| 5-10 | 14S | 10C | 90 | 2.27 | Toluene | 99 | 97 |
| 5-11 | 15S | 11C | 80 | 4.07 | Toluene | 98 | 95 |
| 5-12 | 16S | 12C | 55 | 1.33 | Toluene | 94 | 91 |
| 5-13 | 17S | 13C | 100 | 3.20 | Xylene | 98 | 98 |
| 5-14 | 18S | 14C | 60 | 1.91 | Toluene | 97 | 98 |
| 5-15 | 19S | 15C | 50 | 1.89 | Heptane | 95 | 94 |
| 5-16 | 20S | 16C | 80 | 2.04 | Chlorobenzene | 95 | 93 |
| 5-17 | 15S | 17C | 70 | 2.55 | Toluene | 95 | 93 |
| 5-18 | 10S | 18C | 80 | 3.20 | Xylene | 96 | 93 |

Comparative Example 1

N-(1-phenyl-2,2-dimethyl)ethylidene-2-methoxyethylamine (20.6 g) was dissolved in toluene (60 ml) and chloroacetyl chloride (15.2 g) was dropped into the resulting solution at room temperature. After the completion of dropping, the solution was heated under reflux at ordinary pressure for 4 hours (reflux temperature of 110° C.). When toluene was removed by distillation at a reduced pressure of 2.7×10³ Pa after the completion of the reaction, 27.8 g of the reaction product was obtained. The reaction product was essentially composed of N-(1-phenyl-2,2-dimethyl)ethenyl-N-chloroaceto-2-methoxyethylamide and the purity of the main component of the reaction product was 84%.

Comparative Example 2

N-(1-methylbenzylidene)-2',6'-dimethylaniline (4.57 g) was dissolved in toluene (50 ml), triethylamine (2.20 g) was added to the resulting solution in an iced bath, and a toluene solution (10 ml) of chloroacetyl chloride (2.48 g) was dropped into the solution at room temperature. After the completion of dropping, the solution was heated under reflux at ordinary pressure for 2 hours (reflux temperature of 110° C.). After the completion of the reaction, the reaction mixture was cooled, the produced precipitate was separated by filtration, the filtrate was washed with an aqueous solution of sodium bicarbonate and water, and the organic layer was dried with soda sulfuric anhydride and concentrated under vacuum. When the thus obtained product was re-crystallized with a benzene/hexane mixture solvent, N-(1-phenyl)ethenyl-N-chloroaceto-2',6'-dimethylanilide having a purity of 96% was obtained at an yield of 75%.

EXAMPLE 6

The reaction was carried out using N-(1-phenyl-2-methyl)ethylidene-2-methoxyethylamine (78.9 g) in the same manner as in Example 3 except that a nitrogen gas was blown into a reaction solution during reaction at a rate of 0.8 l/hr. N-(1-phenyl-2-methyl)ethenyl-N-chloroaceto-2-ethoxyethylamide having a purity of 99% was obtained at a yield of 99%.

EXAMPLE 7

The reaction was carried out using N-(1-phenyl-2,2-dimethyl)ethylidene-2-ethoxyethylamine (87.6 g) in the same manner as in Example 4 except that a nitrogen gas was blown into a reaction solution during reaction at a rate of 0.4 l/hr. N-(1-phenyl-2,2-dimethyl)ethenyl-N-chloroaceto-2-ethoxyethylamide having a purity of 99% was obtained at a yield of 100%.

EXAMPLE 8

The reaction was carried out using N-(1-phenyl-2,2-dimethyl)ethylidene-2-ethoxyethylamine (87.6 g) in the same manner as in Example 4 except that a nitrogen gas was blown into a reactor (top of the reaction solution) during reaction at a rate of 1.0 l/hr. N-(1-phenyl-2,2-dimethyl)ethenyl-N-chloroaceto-2-ethoxyethylamide having a purity of 98.5% was obtained at a yield of 99%.

EXAMPLE 9

Various ethenyl amide compounds represented by the following general formula were prepared in the same manner as in Example 6 or Example 8 while an inert gas was blown into the reaction solution or the reactor (top of the reaction solution) during reaction at a predetermined rate. The reaction temperature, reaction pressure, inert gas flow rate, type of solvent, yield and purity of the product are shown in Table 4.

heteroaryl group having 3 to 8 carbon atoms containing one or two hetero atoms selected from the group consisting of oxygen atom, sulfur atom and nitrogen atom, $R_2$ and $R_3$ are the same or different and each is a hydrogen atom or an alkyl group, or may be bonded together to form a ring, and $R_4$ is a substituted or unsubstituted alkyl group having 1 to 12

TABLE 4

| Example No. | Compound No. Schiff base compound | Compound No. Acyl halide | Reaction temperature (°C.) | Reaction pressure × 10⁴ Pa | Flow amount of inert gas (1/hr)※ | Solvent | Yield of product of formula (3) (%) | Purity of product of formula (3) (%) |
|---|---|---|---|---|---|---|---|---|
| 9-1 | 5S | 1C | 80 | 2.60 | 75 | — | 97 | 99 |
| 9-2 | 6S | 2C | 50 | 3.60 | 0.1 | Benzene | 99 | 98 |
| 9-3 | 7S | 3C | 80 | 4.07 | 0.5* | Toluene | 97 | 99 |
| 9-4 | 10S | 6C | 80 | 1.57 | 25 | Xylene | 100 | 99 |
| 9-5 | 11S | 7C | 70 | 2.76 | 10 | Toluene | 97 | 99 |
| 9-6 | 12S | 8C | 75 | 3.29 | 0.3 | Toluene | 97 | 97 |
| 9-7 | 19S | 15C | 50 | 1.89 | 0.3# | Heptane | 96 | 97 |
| 9-8 | 20S | 16C | 80 | 2.04 | 30 | Chlorobenzene | 97 | 96 |

※In this column, the values with no mark (*) were obtained by use of a nitrogen gas, while the value with the mark (*) was obtained by use of a helium gas and the values with the mark (#) was obtained by introducing an inert gas into a gaseous phase of the reaction system, while the values with no mark (#) were obtained by blowing an inert gas into the reaction mixture.

What is claimed is:

1. A process for producing an ethenyl amide compound, which comprises reacting a Schiff base compound having a carbon atom adjacent to a carbon atom constituting an imino group and at least one hydrogen atom on the carbon atom with an acylhalide at a reduced pressure while removing by-produced hydrogen halide by distillation to produce an ethenyl amide compound having an amide bond in the molecule and a double bond between carbons at α-position and β-position with respect to the nitrogen atom of the amide bond.

2. The process of claim 1, wherein the reaction is carried out in the presence of an inert organic solvent having a boiling point at ordinary pressure of 35° to 200° C.

3. The process of claim 2, wherein the reaction is carried out under reflux of the inert organic solvent.

4. The process of any one of claims 1 to 3, wherein he reaction is carried out by introducing an inert gas into a reaction system.

5. The process of claim 4, wherein the inert gas is blown into the reaction mixture.

6. The process of claim 1, wherein the pressure of the reaction system is $1.3 \times 10^2$ to $1 \times 10^5$ Pa.

7. The process of claim 1, wherein the reaction temperature is 40° to 100° C.

8. The process of claim 4, wherein the inert gas is introduced into the reaction system or the reaction mixture at a rate of 0.01 to 800 l/hr.

9. The process of claim 1, wherein the Schiff base compound is represented by the following formula (1):

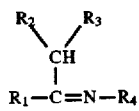

(1)

wherein $R_1$ is a substituted or unsubstituted aryl group having 6 to 14 carbon atoms or a substituted or unsubstituted carbon atoms, a substituted or unsubstituted alkenyl group having 2 to 12 carbon atoms, a substituted or unsubstituted alkinyl group having 2 to 12 carbon atoms, a substituted or unsubstituted aryl group having 6 to 14 carbon atoms, a substituted or unsubstituted heteroaryl group having 3 to 8 carbon atoms, a substituted or unsubstituted cycloalkyl group having 3 to 6 carbon atoms, a substituted or unsubstituted cycloalkenyl group having 4 to 6 carbon atoms, or a substituted or unsubstituted heterocycloalkyl group having 4 to 5 carbon atoms.

10. The process of claim 1, wherein the acylhalide is represented by the following formula (2):

$$R_5COX \qquad (2)$$

wherein $R_5$ is a substituted or unsubstituted alkyl group having 1 to 12 carbon atoms, a substituted or unsubstituted aryl group having 6 to 14 carbon atoms, or a substituted or unsubstituted heteroaryl group having 3 to 8 carbon atoms containing one or two hetero atoms selected from the group consisting of oxygen atom, sulfur atom and nitrogen atom, and X is a halogen atom.

11. The process of claim 1, wherein the ethenyl amide compound is represented by the following formula (3):

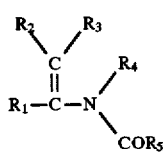

(3)

wherein $R_1$, $R_2$, $R_3$, $R_4$ and $R_5$ are defined the same as in the above general formulas.

* * * * *